(12) United States Patent
Saleem

(10) Patent No.: US 12,409,280 B2
(45) Date of Patent: Sep. 9, 2025

(54) HEATING SMOKEABLE MATERIAL

(71) Applicant: British American Tobacco (Investments) Limited, London (GB)

(72) Inventor: Fozia Saleem, London (GB)

(73) Assignee: British American Tobacco (Investments) Limited, London (GB)

( * ) Notice: Subject to any disclaimer, the term of this patent is extended or adjusted under 35 U.S.C. 154(b) by 772 days.

(21) Appl. No.: 16/948,934

(22) Filed: Oct. 6, 2020

(65) Prior Publication Data

US 2021/0170116 A1      Jun. 10, 2021

Related U.S. Application Data

(63) Continuation of application No. 14/779,210, filed as application No. PCT/EP2014/055485 on Mar. 19, 2014, now abandoned.

(30) Foreign Application Priority Data

Mar. 22, 2013    (GB) ..................................... 1305294

(51) Int. Cl.
*A24F 40/46*        (2020.01)
*A61M 11/04*       (2006.01)
*A61M 15/06*       (2006.01)
*H05B 3/00*         (2006.01)
*H05B 3/06*         (2006.01)
*H05B 3/44*         (2006.01)
(Continued)

(52) U.S. Cl.
CPC ........... *A61M 11/042* (2014.02); *A24F 40/46* (2020.01); *A61M 15/06* (2013.01); *H05B 3/0014* (2013.01); *H05B 3/06* (2013.01); *H05B 3/44* (2013.01); *A24F 40/20* (2020.01); *A61M 2016/0015* (2013.01); *A61M 2205/3368* (2013.01); *A61M 2205/3633* (2013.01); *A61M 2205/3653* (2013.01); *A61M 2205/8206* (2013.01); *H05B 2203/013* (2013.01); *H05B 2203/021* (2013.01); *H05B 2203/022* (2013.01)

(58) Field of Classification Search
None
See application file for complete search history.

(56) References Cited

U.S. PATENT DOCUMENTS 5,233,166 A    8/1993  Maeda et al.
5,264,681 A    11/1993 Nozaki et al.
(Continued)

FOREIGN PATENT DOCUMENTS

CN    102595943 A    7/2012
CN    102781266 A    11/2012
(Continued)

OTHER PUBLICATIONS

Borisova A L., et al., "Reactions of Boron and Aluminum Nitrides,and Materials Based on Them, With Refractory Metals, " 5 pages.
(Continued)

*Primary Examiner* — Katherine A Will
(74) *Attorney, Agent, or Firm* — MERCHANT & GOULD P.C.

(57) ABSTRACT

An apparatus configured to heat smokeable material so as to volatilize at least one of its components for inhalation comprises at least one heating element on or in a substrate material.

13 Claims, 8 Drawing Sheets

(51) Int. Cl.
 *A24F 40/20* (2020.01)
 *A61M 16/00* (2006.01)

(56) References Cited

U.S. PATENT DOCUMENTS

| | | | |
|---|---|---|---|
| 5,322,075 | A | 6/1994 | Deevi et al. |
| 5,408,574 | A | 4/1995 | Deevi et al. |
| 5,468,936 | A | 11/1995 | Deevi et al. |
| 5,573,692 | A | 11/1996 | Das et al. |
| 5,878,752 | A | 3/1999 | Adams et al. |
| 6,084,220 | A | 7/2000 | Suematsu et al. |
| 7,374,063 | B2 | 5/2008 | Reid |
| 2002/0079377 | A1 | 6/2002 | Nichols |
| 2003/0150451 | A1* | 8/2003 | Shayan ............... A61M 11/042 128/203.12 |
| 2003/0183616 | A1 | 10/2003 | Goto |
| 2006/0267724 | A1 | 11/2006 | Parsons |
| 2010/0200006 | A1 | 8/2010 | Robinson et al. |
| 2011/0126848 | A1 | 6/2011 | Zuber et al. |
| 2014/0064715 | A1* | 3/2014 | Greim ................. F24H 1/0018 392/394 |
| 2015/0272219 | A1 | 10/2015 | Hatrick et al. |
| 2016/0295922 | A1 | 10/2016 | John et al. |
| 2017/0055575 | A1 | 3/2017 | Wilke et al. |
| 2017/0055580 | A1 | 3/2017 | Blandino et al. |
| 2017/0055581 | A1 | 3/2017 | Wilke et al. |
| 2017/0055582 | A1 | 3/2017 | Blandino et al. |
| 2017/0055583 | A1 | 3/2017 | Blandino et al. |
| 2017/0055584 | A1 | 3/2017 | Blandino et al. |

FOREIGN PATENT DOCUMENTS

| | | | |
|---|---|---|---|
| DE | 2548019 | A1 | 5/1976 |
| EP | 0653898 | A2 | 5/1995 |
| EP | 0914021 | A2 | 5/1999 |
| EP | 2316286 | A1 * | 5/2011 ........... A24B 15/167 |
| EP | 2327318 | A1 | 6/2011 |
| EP | 2468117 | A1 | 6/2012 |
| EP | 2975951 | A1 | 1/2016 |
| GB | 2446440 | A | 8/2008 |
| GB | 2504075 | A | 1/2014 |
| GB | 2504076 | A | 1/2014 |
| JP | H04324276 | A | 11/1992 |
| JP | H07192906 | A | 7/1995 |
| JP | 3192677 | B2 | 7/2001 |
| JP | 2003293869 | A | 10/2003 |
| JP | 2007080892 | A | 3/2007 |
| JP | 4324276 | B2 | 9/2009 |
| JP | 2013509160 | A | 3/2013 |
| WO | WO-9406314 | A1 | 3/1994 |
| WO | WO-9527412 | A1 | 10/1995 |
| WO | WO-2011063970 | A1 | 6/2011 |
| WO | WO-2012134117 | A2 | 10/2012 |
| WO | 2013034460 | A1 | 3/2013 |
| WO | WO-2013034459 | A1 | 3/2013 |
| WO | WO-2013110211 | A1 | 8/2013 |
| WO | WO-2013148810 | A1 | 10/2013 |
| WO | WO-2014012905 | A1 | 1/2014 |
| WO | WO-2014037794 | A2 | 3/2014 |
| WO | WO-2014048745 | A1 | 4/2014 |

OTHER PUBLICATIONS

Communication pursuant to Article 94(3) EPC for European Application No. 18210216.0, mailed on Oct. 19, 2020, 6 pages.
Examination Report mailed Oct. 26, 2017 for European Application No. 14717683.8, 5 pages.
Extended European Search Report for Application No. 18210216.0, mailed on May 9, 2019, 8 pages.
International Preliminary Report on Patentability for Application No. PCT/EP2014/055485, mailed on Oct. 1, 2015, 11 pages.
International Search Report and Written Opinion for Application No. PCT/EP2014/055485, mailed on Jul. 31, 2014, 16 pages.
Office Action dated Sep. 30, 2019 for Chinese Application No. 201480017532.4filed Mar. 19, 2014, 20 pages.
Office Action mailed Jan. 11, 2017 for Korean Application No. 10-2015-7025842, 25 pages (67 pages with translation).
Office Action mailed Dec. 18, 2018 for Japanese Application No. 2017-172628, 4 pages.
Office Action mailed Aug. 23, 2016 for Japanese Application No. 2016-503647, 3 pages.
Office Action mailed Aug. 25, 2020 for Japanese Application No. JP 2017-172628, 8 pages.
Search report dated Sep. 23, 2019 for Chinese Application No. 201480017532.4 filed Mar. 19, 2014, 2 pages.
Ye zonglin., "Household Electric Appliance Introduction," Light Industry Press, Mar. 1983, First Edition, pp. 74-78.
Monma, et al., "Densification of Tungsten Conductors in Cofired Aluminum Nitride Multilayer Substrates by the Addition of Manganese Oxide", Ceramic Microstructure, Control at the Atomic Level, 1998, pp. 399-406.
Office Action received for Brazilian Patent Application No. 122020008661-0, mailed on May 3, 2021, 5 pages (2 pages of English Translation and 3 pages of Official Copy).
Office Action received for Chinese Patent Application No. 201480017532.4, mailed on Mar. 9, 2021, 16 pages (7 pages of English Translation and 9 pages of Official Copy).
Office Action received for Korean Patent Application No. 10-2017-7037837, mailed on Mar. 23, 2021, 21 pages (2 pages of English Translation and 19 pages of Official Copy).
Office Action received for the Brazilian Patent Application No. 112015024250-2, mailed on Feb. 10, 2021, 5 pages (2 pages of English Translation and 3 pages of Official Copy).
Extended European Search Report received for European Patent Application No. 20205048.0, mailed on Mar. 5, 2021, 11 pages.
Final Written Submissions to the opposition proceedings by HGF for European Patent Application No. 14717683.8, mailed on Apr. 23, 2021, 15 pages.
Reasons for Refusal received for Japanese Patent Application No. 2017-172628, mailed on Mar. 16, 2021, 8 pages (4 pages of English Translation and 4 pages of Official Copy).
Response to the Opposition by the 1st Opponent—JT International for European Patent Application No. 14717683.8, mailed on Apr. 23, 2021, 5 pages.
Response to the Opposition by the proprietor for European Patent Application No. 14717683.8, mailed on Apr. 20, 2021, 22 pages.
Response to the Opposition to the 2nd Opponent—Nerudia for European Patent Application No. 14717683.8, mailed on Apr. 23, 2021, 8 pages.
Notice of Opposition received for European Patent Application No. 20205048.0, mailed on Jul. 22, 2024, 54 pages.

* cited by examiner

HEATING SMOKEABLE MATERIAL

PRIORITY CLAIM

This application is a continuation application of U.S. patent application Ser. No. 14/779,210, filed Sep. 22, 2015, which is the National Stage of International Application No. PCT/EP2014/055485, filed Mar. 19, 2014, which in turn claims priority to and benefit of United Kingdom Patent Application No. GB1305294.9, filed Mar. 22, 2013. The entire contents of the aforementioned applications are herein expressly incorporated by reference.

FIELD

The invention relates to heating smokeable material.

BACKGROUND

Smoking articles such as cigarettes and cigars burn tobacco during use to create tobacco smoke. Attempts have been made to provide alternatives to these smoking articles by creating products which release compounds without creating tobacco smoke. Examples of such products are so-called heat-not-burn products which release compounds by heating, but not burning, tobacco.

SUMMARY

According to the invention, there is provided a smokeable material heating apparatus comprising a substrate and at least one printed heating element arranged to heat the substrate to a smokeable material volatilizing temperature and thereby cause the substrate to volatilize at least one component of smokeable material for inhalation.

The heating element may be located at least partially inside the substrate.

The coefficient of thermal expansion of the heating element may be substantially equal to the coefficient of thermal expansion of the substrate.

The heating element may be chemically bonded to the substrate.

The heating element and the substrate may comprise a single sintered structure.

The heating element may comprise an electrically resistive trace in the substrate.

The substrate may comprise a ceramics material.

The substrate may be proximal a smokeable material heating chamber configured to contain the body of smokeable material during heating.

The apparatus may comprise a plurality of the heating elements arranged in layers inside the substrate.

The layers of heating elements may be interconnected by heating element vias through the substrate.

According to the invention, there is also provided an apparatus comprising a heater configured to heat smokeable material to volatilize at least one component of the smokeable material for inhalation, wherein the heater comprises a substrate and a heating element with substantially equal coefficients of thermal expansion.

The heating element may be printed to the substrate.

The heating element may be arranged to heat the substrate to a temperature sufficient for the substrate to volatilize at least one component of smokeable material located in an adjacent smokeable material heating chamber.

The heating element may be located at least partially inside the substrate.

The heating element may be chemically bonded to the substrate.

The heater may comprise a sintered structure comprising the heating element and the substrate.

The heating element may comprise an electrically resistive trace in the substrate and/or the substrate may comprise a ceramics material.

The apparatus may comprise a plurality of the heating elements arranged in layers inside the substrate.

The layers of heating elements may be interconnected by heating element vias through the substrate.

According to the invention, there is also provided an apparatus comprising a heater configured to heat smokeable material to volatilize at least one component of the smokeable material for inhalation, wherein the heater comprises a multiply layered structure of ceramic material and electrically resistive heating elements.

The heating elements may comprise electrically resistive traces in the ceramic material.

The heating elements may be chemically bonded to the ceramic material in a sintered structure.

The coefficient of thermal expansion of the ceramic material may be substantially equal to the coefficient of thermal expansion of the heating elements.

The heating elements may comprise Tungsten and the ceramic material may comprise Aluminum Nitride Ceramic.

The heating elements may be printed to the substrate.

The heating elements may be arranged to heat the ceramic material to a temperature sufficient to volatilize at least one component of smokeable material located in a heating chamber adjacent the ceramic material.

The heating elements may be located inside the ceramic material.

Layers of the heating elements may be interconnected by heating element vias through the ceramic material.

According to the invention, there is also provided an apparatus comprising a heater arranged to heat smokeable material, wherein the heater comprises a substrate and at least one heating element located inside the substrate so as to heat the substrate to cause the substrate to volatilize at least one component of the smokeable material for inhalation.

The heater may comprise a thermal expansion-matching structure.

The coefficient of thermal expansion of the heating element may be substantially equal to the coefficient of thermal expansion of the substrate.

The heating element and the substrate may be sintered to form a chemically bonded structure.

The substrate may comprise a ceramics material and the heating element may comprise an electrically resistive trace material.

The substrate may be proximal a smokeable material heating chamber configured to contain the body of smokeable material during heating.

The apparatus may comprise a plurality of the heating elements arranged in layers inside the substrate.

The layers of heating elements may be interconnected by heating element vias through the substrate.

The apparatus may be configured to heat the smokeable material to a smokeable material volatilizing temperature of at least 120 degrees Celsius.

The apparatus may be configured to heat the smokeable material to a smokeable material volatilizing temperature of between 120 degrees Celsius and 250 degrees Celsius.

The apparatus may be configured to heat the smokeable material to a smokeable material volatilizing temperature of between 130 degrees Celsius and 180 degrees Celsius.

The invention may facilitate use of at least one printed heating element to heat a substrate to a smokeable material volatilizing temperature and thereby cause the substrate to volatilize at least one component of smokeable material for inhalation.

The invention may facilitate use of a heater comprising a substrate and a heating element with substantially equal coefficients of thermal expansion to heat smokeable material to volatilize at least one component of the smokeable material for inhalation.

The invention may facilitate use of a heater comprising a multiply layered structure of ceramic material and electrically resistive heating elements to heat smokeable material to volatilize at least one component of the smokeable material for inhalation.

The invention may facilitate use of a heater comprising a substrate and at least one heating element located inside the substrate to heat the substrate and cause the substrate to volatilize at least one component of smokeable material for inhalation.

According to the invention, there is provided a method of heating smokeable material, comprising heating a substrate to a smokeable material volatilizing temperature using at least one printed heating element arranged to heat the substrate and causing the heated substrate to volatilize at least one component of smokeable material for inhalation.

According to the invention, there is provided a method of heating smokeable material, comprising heating a substrate to a smokeable material volatilizing temperature using at least one heating element located inside the substrate and causing the heated substrate to volatilize at least one component of smokeable material for inhalation.

For exemplary purposes only, embodiments of the invention are described below with reference to the accompanying figures in which:

DETAILED DESCRIPTION

Figure 1:
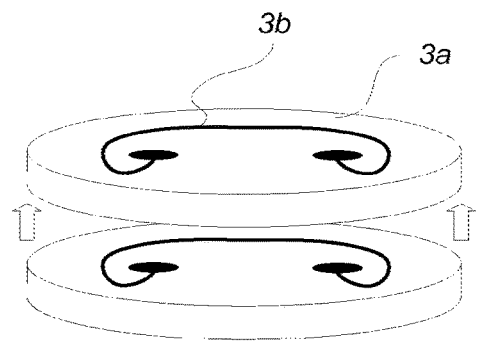
FIG. 1 is a schematic illustration of layers of a smokeable material heater comprising a substrate and heating elements interconnected by vias between the layers.

As used herein, the term 'smokeable material' includes any material that provides volatilized components upon heating and includes any tobacco-containing material and may, for example, include one or more of tobacco, tobacco derivatives, expanded tobacco, reconstituted tobacco or tobacco substitutes.

An apparatus 1 for heating smokeable material comprises an energy source 2, a heater 3 and a heating chamber 4. The energy source 2 may comprise a battery such as a Li-ion battery, Ni battery, Alkaline battery and/or the like, and is electrically coupled to the heater 3 to supply electrical energy to the heater 3 when required. It will be appreciated that, additionally or alternatively to the battery, the energy source 2 could comprise other types of source 2 such as one or more fuel cells and/or another non-battery sources of electricity. The heating chamber 4 is configured to receive smokeable material 5 so that the smokeable material 5 can be heated in the heating chamber 4. For example, the heating chamber 4 may be located adjacent to the heater 3 so that thermal energy from the heater 3 heats the smokeable material 5 therein. Heat from the heater 3 heats the smokeable material 5 to volatilize aromatic compounds and nicotine in the smokeable material 5 without burning the smokeable material 5. The smokeable material 5 may comprise a tobacco blend. A mouthpiece 6 is provided through which a user of the apparatus 1 can inhale the volatilized compounds during use of the apparatus 1.

Figure 2:
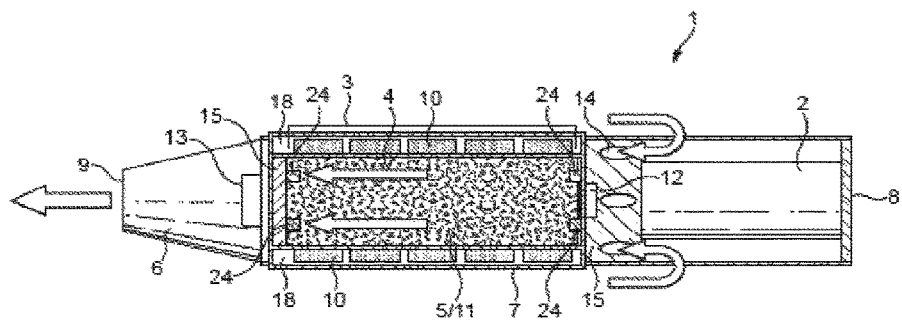
FIG. 2 is a schematic, cross sectional illustration of an apparatus configured to heat smokeable material to release aromatic compounds and/or nicotine from the smokeable material.

A housing 7 may contain components of the apparatus 1 such as the energy source 2 and heater 3. As shown schematically in FIG. 2, the housing 7 may comprise an approximately cylindrical tube with the energy source 2 located towards its first end 8 and the heater 3 and heating chamber 4 located towards its opposite, second end 9. The energy source 2 and heater 3 may extend along the longitudinal axis of the housing 7. For example, as shown in FIG. 2, the energy source 2 and heater 3 can be aligned along the central longitudinal axis of the housing 7 in a substantially end-to-end arrangement so that an end face of the energy source 2 substantially faces an end face of the heater 3. The mouthpiece 6 may be located at the second end 9 of the housing 7, adjacent the heating chamber 4 and smokeable material 5.

The length of the housing 7 may be approximately 130 mm. An example length of the energy source 2 is approximately 59 mm. The length of the heater 3 and heating region 4 may be approximately 50 mm. The depth, for example the diameter, of the heating chamber 4 may be between approximately 5 mm and approximately 15 mm, such as between approximately 8 mm and approximately 10 mm. The diameter of the energy source 2 may be between approximately 10.0 mm and approximately 15.0 mm, such as 14.6 mm. The diameter of the housing 7 may be between approximately 11 mm and approximately 18 mm. For example, the diameter of the housing's first end 8 may be 18 mm whilst the diameter of the mouthpiece 6 at the housing's second end 9 may be 15 mm. Dimensions other than those given above could alternatively be used.

The housing 7 is suitable for being gripped by a user during use of the apparatus 1 so that the user can inhale volatilized smokeable material compounds from the mouthpiece 6 of the apparatus 1.

Heat insulation may be provided between the energy source 2 and the heater 3 to prevent direct transfer of heat from one to the other.

The heater 3 may comprise a printed heater 3. For example, the heater 3 may comprise a substrate 3a and one or more heating elements 3b which may be printed onto or into the substrate 3a. As described below, the heating elements 3b may be configured to heat the substrate 3a at a rapid rate so that the temperature of the substrate 3a substantially matches the temperature of the heating elements 3b during heating of the smokeable material 5.

The substrate 3a may comprise a ceramics material, such as Aluminum Nitride Ceramic, and the heating elements 3b may comprise electrically resistive trace elements 3b which are heated by electrical currents flowing in the elements 3b. For example, the heating elements 3b may comprise an electrically resistive metal such as Tungsten. The currents in the heating elements 3b may be caused by an electromotive force supplied by the energy source 2, which is electrically coupled to the heater 3.

The heating elements 3b are arranged in or on the substrate material 3a so as to heat the substrate 3a. As mentioned above, the arrangement of the heating elements 3b in or on the substrate 3a may be so as to heat the substrate 3a to approximately the same temperature as the heating elements 3b.

The substrate 3a may be heated by the heating elements 3b to a volatilizing temperature of the smokeable material 5 so that heat from the heated substrate 3a causes components of the smokeable material 5 to be volatilized for inhalation through the mouthpiece 6. Therefore, smokeable material 5 in the heating region 4 may be heated by both the heating elements 3b and the heated substrate 3a. The rate at which the temperature of the substrate 3a increases during heating may be substantially the same as the rate at which the temperature of the heating elements 3b increase. Therefore, the temperature of the heating elements 3b and the substrate 3a may be approximately equal during heating of the smokeable material 5.

The arrangement of the heater 3 may be such that the peripheral surfaces of the heater 3 principally comprise those of the heated substrate 3a and, as such, the smokeable material 5 may be heated principally by heat emitted from the heated substrate 3a rather than being heated directly by the heating elements 3b. For example, as described below and shown schematically in FIG. 1, the heating elements 3b may be located principally or entirely inside the substrate 3a and may comprise a plurality of distinct heating layers of heating elements 3b separated by layers of substrate 3a.

The coefficient of thermal expansion of the heating elements 3b may be matched to the coefficient of thermal expansion of the substrate 3a. In particular, the value of the coefficient of thermal expansion of the heating elements 3b may be substantially equal to the value of the coefficient of thermal expansion of the substrate 3a. The heating elements 3b and substrate 3a may therefore together form an expansion-matching heater structure 3.

The matched thermal expansion coefficients of the substrate 3a and heating elements 3b means that thermal expansion of the heating elements 3b is matched by a corresponding expansion in the substrate 3a. Similarly, thermal contraction of the heating elements 3b is matched by a corresponding contraction in the substrate 3a. The expansion-matched nature of structure means that the heater 3 as a whole expands/contracts at substantially the same rate and by the same amount across the entire heater structure during heating/cooling. The expansion and contraction stresses on the heater structure 3 are small and the heater can be caused to undergo rapid, significant and frequent temperature transitions without placing significant material stress on the heater structure 3.

The substrate 3a and the heating elements 3b may be chemically bonded together in the heater structure 3. For example, the chemical bonds between the substrate 3a and the heating elements 3b may be formed during a sintering process, in which the substrate 3a and the heating elements 3b are fused together under the application of heat to create a solid heater structure 3.

More specifically, the chemically bonded heater structure 3 may be manufactured by initially applying liquid heating element material 3b to one or more surfaces of the substrate material 3a, layering the substrate material 3a with the heating element material 3b and sintering the layered assembly to form the bonded heater structure 3. This is illustrated schematically in FIG. 1.

Application of the liquid heating element material 3b can, for example, be carried out by printing the liquid material 3b onto the substrate material 3a. The application of the liquid heating element 3b onto the substrate 3a may be extremely precise so as to achieve very low tolerances, for example in the order of micrometres or nanometres, in the location of the heating element material 3b on the substrate 3a and thereby cause the heating elements 3b to form in very specific desired regions of the substrate 3a. A suitable printing process is to use a screen printer to print the liquid 3b, which may be in the form of an ink, onto the substrate material 3a.

The substrate material 3a may comprise suitable binders and/or plasticizers which aid with the formation of the layered heater structure 3 before the formation of chemical bonds during sintering. Additionally or alternatively, the liquid heating element material 3b may comprise suitable binders and/or plasticizers. These may be of the same composition as the binders and/or plasticizers comprised in the substrate material 3a.

The substrate material 3a onto which the heating element material 3b is applied may comprise pre-sintered layers of substrate 3a, such as pre-sintered sections of ceramic tape, which are built up on top of one another to form a layered structure comprising both the substrate 3a and the heating element material 3b. One or more vias may be formed in the layers of substrate material 3a so that the liquid heating material 3b fills the vias and, ultimately, forms interconnections between the layers of heating elements 3b in the heater 3. In particular, each layer of heating elements 3b may be interconnected to one or more other distinct layers of heating elements 3b by sections of heating element 3b which pass through the vias in the substrate 3a.

The vias may be formed by any suitable process. For example, the vias may be formed by punching holes in the individual layers of substrate 3a before the layers of substrate 3a are layered on top of one another in the heater structure 3. The holes in the layers of substrate 3a may be aligned in the layered structure so that interconnections between a plurality of layers of heating elements 3b are created during sintering. The vias formed between the layers 3b may be of any suitable shape, including three-dimensional shapes.

If desired, a plurality of electrical circuits can be printed onto the substrate 3a in order to provide control signals or measurement signals to/from a controller 12 of the apparatus 1. For example, temperature measurement circuits, which may incorporate one or more Resistance Temperature Detectors (RTD), can be printed onto, adjacent or underneath the heater elements 3b, or elsewhere on the substrate 3a, so that the temperature of the heater 3 can be monitored and adjusted by the controller 12 to obtain desired volatilizing or pre-volatilizing temperatures in the smokeable material 5.

Before the assembly of substrate layers 3a and heating element material 3b is sintered to create the chemical bonds and cohesive nature of the heater 3 referred to above, the assembly may be de-bound of the binders and/or plasticizers referred to previously.

The chemical bonds and the matched thermal expansion coefficients create a robust heater structure 3, which can be repeatedly re-used to heat and volatilize newly-loaded smokeable material 5 in the heating region 4.

The heater 3 can be manufactured into any suitable shape using the layering technique described above. For example, the heater 3 may comprise a substantially hollow cylinder located around the smokeable material heating region 4 so that heat is emitted by the heater 3 in a radially inward direction. An example of this is described below in relation to FIG. 2. Alternatively, the smokeable material heating region 4 may be located around the heater 3. An example is a co-axial arrangement in which the heater 3 emits heat in a radially outward direction into the heating region 4, although other shapes are also possible as will be evident from the discussion below.

A specific example of an expansion matched, chemically bonded heater structure 3 is one in which the heating substrate 3a comprises pre-sintered Aluminum Nitride Ceramic tape and the heating element material 3b comprises Tungsten-containing ink which is screen printed onto the ceramics tape 3a. Once the ceramics tape 3a has been printed with the heating element material 3b and holes have been created to form the vias referred to above, the ceramics tape 3a is layered so as to form a structure containing internal layers of heating element material 3b connected together by vias in the tape 3a. The assembly is then sintered to form a cohesive and chemically-bonded heater 3. During activation of the heater 3, the Aluminum Nitride substrate 3a and Tungsten heating elements 3b expand and contract at a rate of approximately 4.5 parts per million per degree centigrade and thus the heater structure 3 as a whole expands and contracts without placing stress on any particular part of the structure 3.

The thickness of the heater 3 may be small, such as less than 2 mm or less than 1 mm, which can contribute towards reducing the overall dimensions of the apparatus 1 compared to the use of other types of heaters. For example, the heater 3 may have a thickness of between approximately 0.1 mm and 2.0 mm, such as between approximately 0.3 mm and approximately 1.0 mm, although heaters 3 with larger thicknesses such as those up to 6.5 mm are equally possible.

The heater 3 can be operated over a wide range of power outputs in order to heat and maintain the smokeable material 5 in a desired temperature range. For example, the power output of the heater 3 may be in the range of zero to approximately 2000 watts/in$^2$ and may be controllable by the controller 12 of the apparatus 1 so that the temperature of the smokeable material 5 is maintained or adjusted into the desired temperature range. The controller 12 may adjust the power output of the heater 3 based on measurements of temperature inside the heater 3, at the peripheral surfaces of the heater 3 and/or inside the smokeable material 5, using the temperature measurement circuits referred to above.

The controller 12 may cause the heater 3, or distinct regions 10 of the heater 3, to cycle between predetermined set temperatures for predetermined periods of time or may vary the temperature of the heater 3 and/or separate regions 10 of the heater 3 in accordance with a heating regime. The controller 12 and examples of suitable heating regimes are described in more detail below. The heater 3 has a low mass and therefore its use can help to reduce the overall mass of the apparatus 1.

As shown in FIG. 2 and referred to briefly above, the heater 3 may comprise a plurality of individual heating regions 10. The heating regions 10 may be operable independently of one another so that different regions 10 can be activated at different times to heat the smokeable material 5. This may be achieved by activating heating elements 3b located in particular regions 10 of the heater 3 at different times. The heating regions 10 may be arranged in the heater 3 in any geometric arrangement. However, in the example shown in FIG. 2, the heating regions 10 are geometrically arranged in the heater 3 so that different ones of the heating regions 10 are arranged to predominately and independently heat different regions of the smokeable material 5.

For example, referring to FIG. 2, the heater 3 may comprise a plurality of axially aligned heating regions 10 in a substantially elongate arrangement. The regions 10 may each comprise an individual section of the heater 3, such as an independently temperature-controllable section of the bonded substrate 3a and heating elements 3b structure 3 described above. The heating regions 10 may, for example, all be aligned with each other along a longitudinal axis of the heater 3, thus providing a plurality of independent heating zones along the length of the heater 3.

Referring to FIG. 2, each heating region 10 may comprise a hollow heating cylinder 10, which may be a ring 10, having a finite length which is significantly less than the length of the heater 3 as a whole. The arrangement of axially aligned heating regions 10 define the exterior of the heating chamber 4 and are configured to heat smokeable material 5 located in the heating chamber 4. As mentioned previously, the heat is applied inwardly, predominately towards the central longitudinal axis of the heating chamber 4. The heating regions 10 are arranged with their radial, or otherwise transverse, surfaces facing one another along the length of the heater 3. The transverse surfaces of each heating region 10 may optionally be separated from the transverse surfaces of their neighboring heating region(s) 10 by thermal insulation 18, as shown in FIG. 2 and described below, or may connected and/or contiguous with their neighboring heating region(s) 10.

Figure 3:
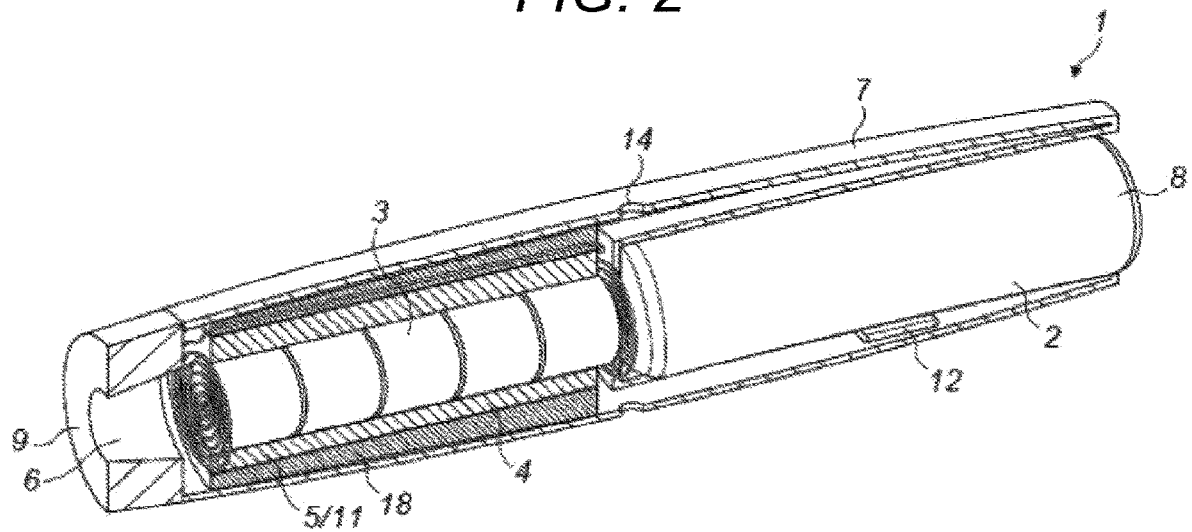
FIG. 3 is a perspective, partially cut-away illustration of an apparatus configured to heat smokeable material to release aromatic compounds and/or nicotine from the smokeable material.
Figure 4:
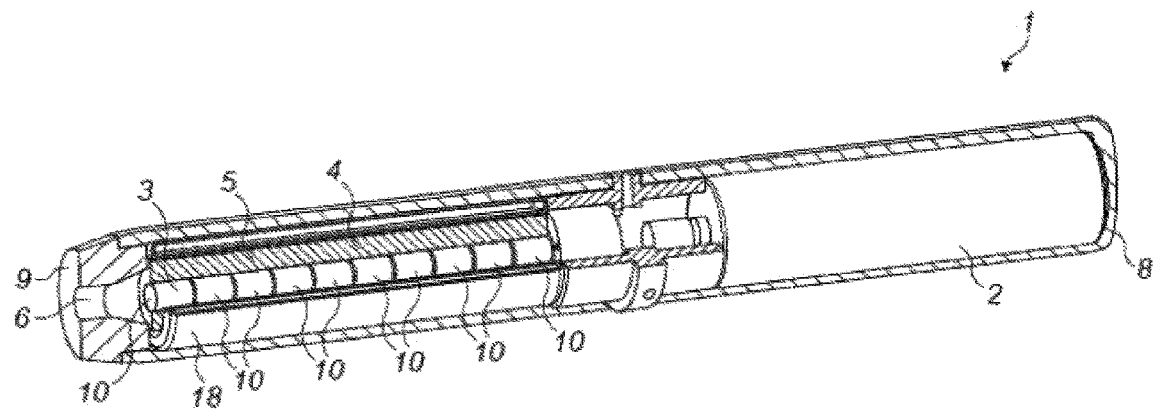
FIG. 4 is a perspective, partially cut-away illustration of an apparatus configured to heat smokeable material, in which the smokeable material is provided around an elongate heater divided into radial heating sections.

As shown in FIGS. 2 and 3, the heater 3 may alternatively be located in a central region of the housing 7 and the heating chamber 4 and smokeable material 5 may be located around the longitudinal surface of the heater 3. In this arrangement, thermal energy emitted by the heater 3 travels outwards from the longitudinal surface of the heater 3 into the heating chamber 4 and the smokeable material 5.

The heating regions 10 may each comprise an individual section of the heater 3. As shown in FIGS. 1 to 4, each heating region 10 may comprise a heating cylinder 10 having a finite length which is significantly less than the length of the heater 3 as a whole. However, other configurations of heater 3 could alternatively be used and so the use of cylindrical sections of heater 3 is not required. The heating regions 10 may be arranged with their transverse surfaces facing one another along the length of the heater 3. The transverse surfaces of each region 10 may touch the transverse surfaces of its neighboring regions 10. Alternatively, a heat insulating or heat reflecting layer may be present between the transverse surfaces of the regions 10 so that thermal energy emitted from each one of the regions 10 does not substantially heat the neighboring regions 10 and instead travels predominately into the heating chamber 4 and smokeable material 5. Each heating region 10 may have substantially the same dimensions as the other regions 10.

In this way, when a particular one of the heating regions 10 is activated, it supplies thermal energy to the smokeable material 5 located adjacent, for example radially adjacent, the heating region 10 without substantially heating the remainder of the smokeable material 5. Referring to FIG. 3, the heated region of smokeable material 5 may comprise a ring of smokeable material 5 located around the heating region 10 which has been activated. The smokeable material 5 can therefore be heated in independent sections, for example rings or substantially solid cylinders, where each section corresponds to smokeable material 5 located directly adjacent a particular one of the heating regions 10 and has a mass and volume which is significantly less than the body of smokeable material 5 as a whole.

Additionally or alternatively, the heater 3 may comprise a plurality of elongate, longitudinally extending heating regions 10 positioned at different locations around the central longitudinal axis of the heater 3. The heating regions 10 may be of different lengths, or may be of substantially the same length so that each extends along substantially the whole length of the heater 3.

The heated sections of smokeable material 5 may comprise longitudinal sections of smokeable material 5 which lie parallel and directly adjacent to the longitudinal heating regions 10. Therefore, as explained previously, the smokeable material 5 can be heated in independent sections.

As will be described further below, the heating regions 10 can each be individually and selectively activated.

The smokeable material 5 may be comprised in a cartridge 11 which can be inserted into the heating chamber 4. For example, as shown in FIG. 2, the cartridge 11 can comprise a substantially solid body of smokeable material 5 such as a cylinder which fits into a recess of the heater 3. In this configuration, the external surface of the smokeable material body faces the heater 3. Alternatively, as shown in FIG. 3, the cartridge 11 can comprise a smokeable material tube 11 which can be inserted around the heater 3 so that the internal surface of the smokeable material tube 11 faces the longitudinal surface of the heater 3. The smokeable material tube 11 may be hollow. The diameter of the hollow centre of the tube 11 may be substantially equal to, or slightly larger than, the diameter or otherwise transverse dimension of the heater 3 so that the tube 11 is a close fit around the heater 3. The length of the cartridge 11 may be approximately equal to the length of the heater 3 so that the heater 3 can heat the cartridge 11 along its whole length.

The housing 7 of the apparatus 1 may comprise an opening through which the cartridge 11 can be inserted into the heating chamber 4. The opening may, for example, comprise an opening located at the housing's second end 9 so that the cartridge 11 can be slid into the opening and pushed directly into the heating chamber 4. The opening is preferably closed during use of the apparatus 1 to heat the smokeable material 5. Alternatively, a section of the housing 7 at the second end 9 is removable from the apparatus 1 so that the smokeable material 5 can be inserted into the heating chamber 4. The apparatus 1 may optionally be equipped with a user-operable smokeable material ejection unit, such as an internal mechanism configured to slide used smokeable material 5 off and/or away from the heater 3. The used smokeable material 5 may, for example, be pushed back through the opening in the housing 7. A new cartridge 11 can then be inserted as required.

Figure 5:
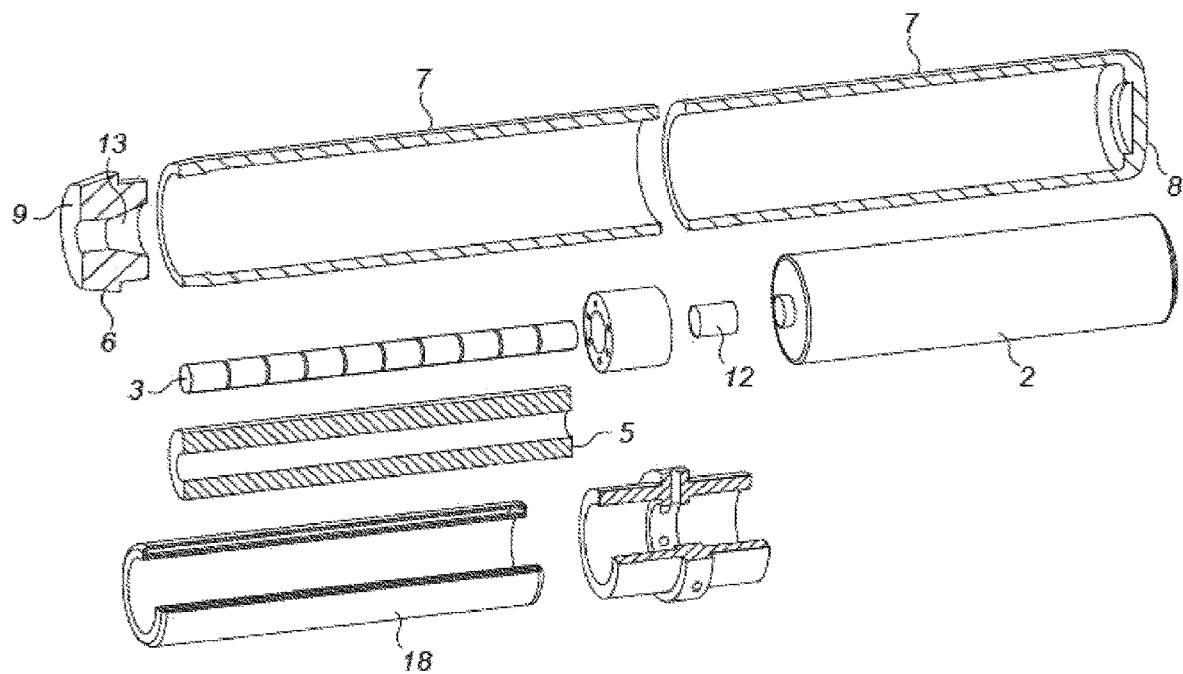
FIG. 5 is an exploded, partially cut-away view of an apparatus configured to heat smokeable material, in which the smokeable material is provided around an elongate heater divided into radial heating sections.

As mentioned previously, the apparatus 1 may comprise a controller 12, such as a microcontroller 12, which is configured to control operation of the apparatus 1. The controller 12 is electronically connected to the other components of the apparatus 1 such as the energy source 2 and heater 3 so that it can control their operation by sending and receiving signals. The controller 12 is, in particular, configured to control activation of the heater 3 to heat the smokeable material 5. For example, the controller 12 may be configured to activate the heater 3, which may comprise selectively activating one or more heating regions 10, in response to a user drawing on the mouthpiece 6 of the apparatus 1. In this regard, the controller 12 may be in communication with a puff sensor 13 via a suitable communicative coupling. The puff sensor 13 is configured to detect when a puff occurs at the mouthpiece 6 and, in response, is configured to send a signal to the controller 12 indicative of the puff. An electronic signal may be used. The controller 12 may respond to the signal from the puff sensor 13 by activating the heater 3 and thereby heating the smokeable material 5. The use of a puff sensor 13 to activate the heater 3 is not, however, essential and other means for providing a stimulus to activate the heater 3 can alternatively be used. For example, the controller 12 may activate the heater 3 in response to another type of activation stimulus such as actuation of a user-operable actuator. The volatilized compounds released during heating can then be inhaled by the user through the mouthpiece 6. The controller 12 can be located at any suitable position within the housing 7. An example position is between the energy source 2 and the heater 3/heating chamber 4, as illustrated in FIG. 5.

If the heater 3 comprises two or more heating regions 10 as described above, the controller 12 may be configured to activate the heating regions 10 in a predetermined order or pattern. For example, the controller 12 may be configured to activate the heating regions 10 sequentially along or around the heating chamber 4. Each activation of a heating region 10 may be in response to detection of a puff by the puff sensor 13 or may be triggered in an alternative way, as described further below.

Figure 6:
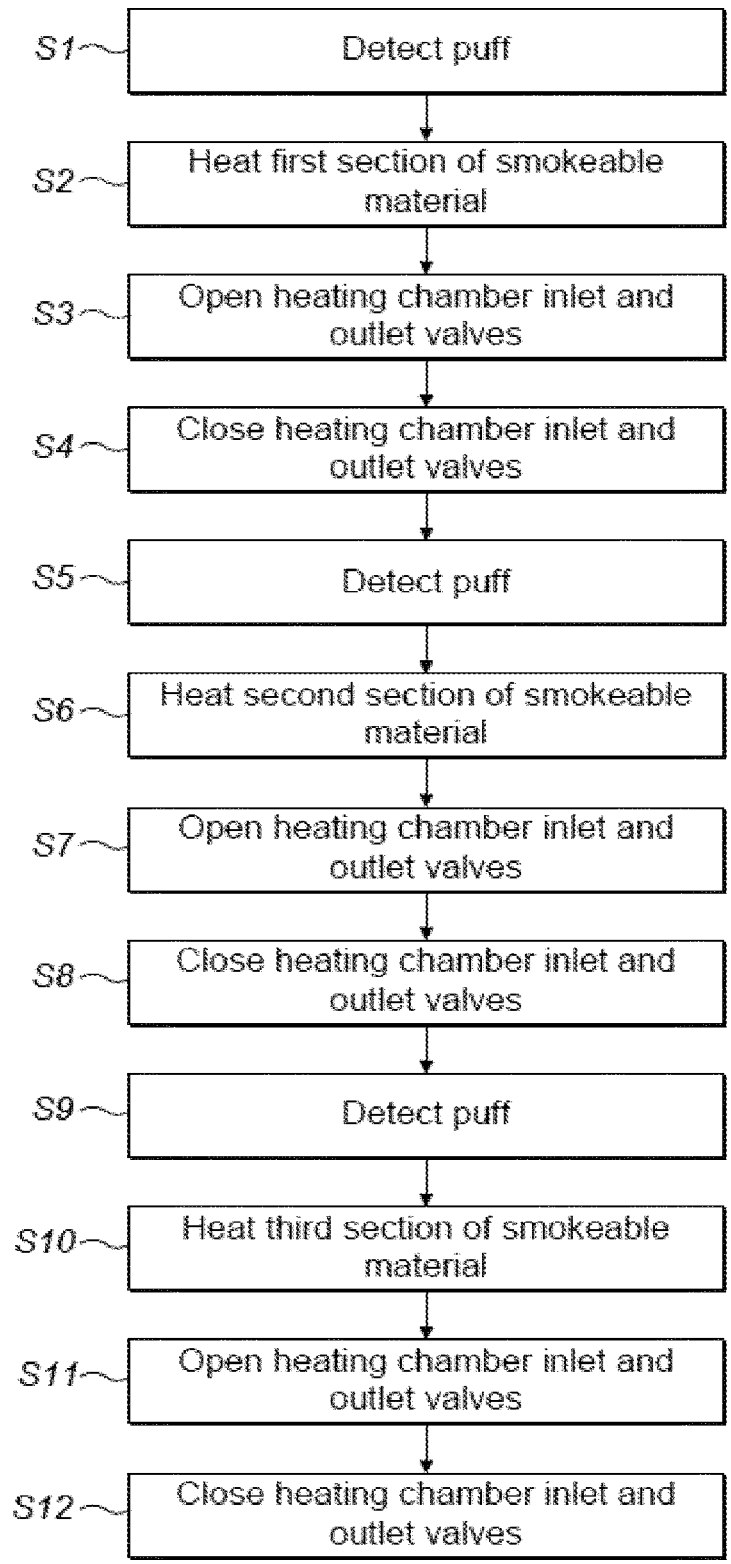
FIG. 6 is a flow diagram showing a method of activating heating regions and opening and closing heating chamber valves during puffing.

Referring to FIG. 6, an example heating method may comprise a first step S1 in which an activation stimulus such as a first puff is detected followed by a second step S2 in which a first section of smokeable material 5 is heated in response to the first puff or other activation stimulus. In a third step S3, hermetically sealable inlet and outlet valves 24 may be opened to allow air to be drawn through the heating chamber 4 and out of the apparatus 1 through the mouthpiece 6. In a fourth step S4, the valves 24 are closed. These valves 24 are described in more detail below with respect to FIG. 30. In fifth S5, sixth S6, seventh S7 and eighth S8 steps, a second section of smokeable material 5 may be heated in response to a second activation stimulus such as a second puff, with a corresponding opening and closing of the heating chamber inlet and outlet valves 24. In ninth S9, tenth S10, eleventh S11 and twelfth S12 steps, a third section of the smokeable material 5 may be heated in response to a third activation stimulus such as a third puff with a corresponding opening and closing of the heating chamber inlet and outlet valves 24, and so on. As referred to above, means other than a puff sensor 13 could alternatively be used. For example, a user of the apparatus 1 may actuate a control switch to indicate that he/she is taking a new puff. In this way, a fresh section of smokeable material 5 may be heated to volatilize nicotine and aromatic compounds for each new puff. The number of heating regions 10 and/or independently heatable sections of smokeable material 5 may correspond to the number of puffs for which the cartridge 11 is intended to be used. Alternatively, each independently heatable smokeable material section 5 may be heated by its corresponding heating region(s) 10 for a plurality of puffs such as two, three or four puffs, so that a fresh section of smokeable material 5 is heated only after a plurality of puffs have been taken whilst heating the previous smokeable material section.

Instead of activating each heating region 10 in response to an individual puff, the heating regions 10 may alternatively be activated sequentially, one after the other, in response to a single, initial puff at the mouthpiece 6. For example, the heating regions 10 may be activated at regular, predetermined intervals over the expected inhalation period for a particular smokeable material cartridge 11. The inhalation period may, for example, be between approximately one and approximately four minutes. Therefore, at least the fifth and ninth steps S5, S9 shown in FIG. 6 are optional. Each heating region 10 may be activated for a predetermined period corresponding to the duration of the single or plurality of puffs for which the corresponding independently heatable smokeable material section 5 is intended to be heated. Once all of the heating regions 10 have been activated for a particular cartridge 11, the controller 12 may be configured to indicate to the user that the cartridge 11 should be changed. The controller 12 may, for example, activate an indicator light at the external surface of the housing 7.

It will be appreciated that activating individual heating regions 10 in order rather than activating the entire heater 3 means that the energy required to heat the smokeable material 5 is reduced over what would be required if the heater 3 were activated fully over the entire inhalation period of a cartridge 11. Therefore, the maximum required power output of the energy source 2 is also reduced. This means that a smaller and/or lighter energy source 2 can be installed in the apparatus 1.

Figure 8:
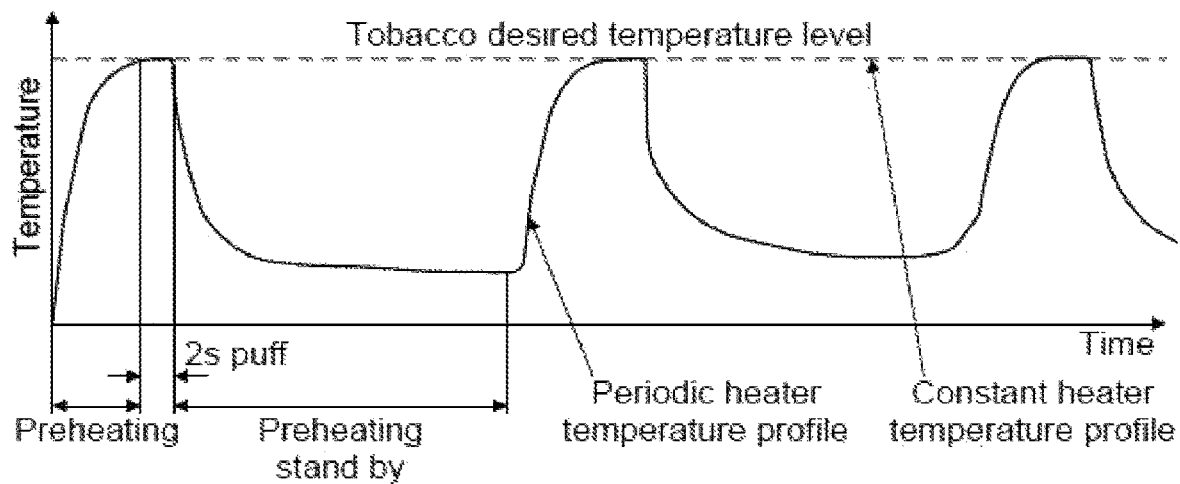
FIG. 8 is a graphical illustration of a heating pattern which can be used to heat smokeable material using a heater.

The controller 12 may be configured to de-activate the heater 3, or reduce the power being supplied to the heater 3, in between puffs. This saves energy and extends the life of the energy source 2. For example, upon the apparatus 1 being switched on by a user or in response to some other stimulus, such as detection of a user placing their mouth against the mouthpiece 6, the controller 12 may be configured to cause the heater 3, or next heating region 10 to be used to heat the smokeable material 5, to be partially activated so that it heats up in preparation to volatilize components of the smokeable material 5. The partial activation does not heat the smokeable material 5 to a sufficient temperature to volatilize nicotine. A suitable temperature could be less than 120° C., such as approximately 100° C. In response to detection of a puff by the puff sensor 13, the controller 12 can then cause the heater 3 or heating region 10 in question to heat the smokeable material 5 further in order to rapidly volatilize the nicotine and other aromatic compounds for inhalation by the user. If the smokeable material 5 comprises tobacco, a suitable temperature for volatilizing the nicotine and other aromatic compounds may be above 120° C., such between 150° C. and 250° C. or between 130° C. and 180° C. Therefore, examples of full activation temperatures include 180° C. and 250° C. A super-capacitor can optionally be used to provide the peak current used to heat the smokeable material 5 to the volatilization temperature. An example of a suitable heating pattern is shown in FIG. 8, in which the peaks may respectively represent the full activation of different heating regions 10. As can be seen, the smokeable material 5 is maintained at the volatilization temperature for the approximate period of the puff which, in this example, is two seconds.

Three example operational modes of the heater 3 are described below.

In a first operational mode, during full activation of a particular heating region 10, all other heating regions 10 of the heater are deactivated. Therefore, when a new heating region 10 is activated, the previous heating region is deactivated. Power is supplied only to the activated region 10.

Alternatively, in a second operational mode, during full activation of a particular heating region 10, one or more of the other heating regions 10 may be partially activated. Partial activation of the one or more other heating regions 10 may comprise heating the other heating region(s) 10 to a temperature which is sufficient to substantially prevent condensation of components such as nicotine volatilized from the smokeable material 5 in the heating chamber 4. The temperature of the heating regions 10 which are partially activated is less than the temperature of the heating region 10 which is fully activated. The smokeable material 10 located adjacent the partially activated regions 10 is not heated to a temperature sufficient to volatilize components of the smokeable material 5.

Alternatively, in a third operational mode, once a particular heating region 10 has been activated, it remains fully activated until the heater 3 is switched off Therefore, the power supplied to the heater 3 incrementally increases as more of the heating regions 10 are activated during inhalation from the cartridge 11. As with the second mode previously described, the continuing activation of the heating regions 10 substantially prevent condensation of components such as nicotine volatilized from the smokeable material 5 in the heating chamber 4.

Figure 15:
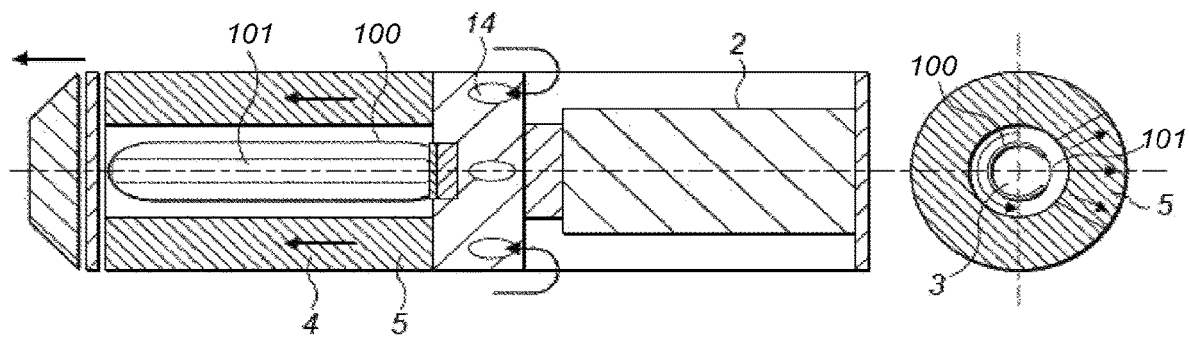
FIG. 15 is a schematic, cross-sectional illustration of a heat shield and a heat-transparent window which are moveable relative to a body of smokeable material to selectively allow thermal energy to be transmitted to different sections of the smokeable material through the window.

The apparatus 1 may comprise a heat shield 100, which is located between the heater 3 and the heating chamber 4/smokeable material 5. The heat shield 100 is configured to substantially prevent thermal energy from flowing through the heat shield 100 and therefore can be used to selectively prevent the smokeable material 5 from being heated even when the heater 3 is activated and emitting thermal energy. Referring to FIG. 15, the heat shield 100 may, for example, comprise a cylindrical layer of heat reflective material which is located co-axially around the heater 3. Alternatively, if the heater 3 is located around the heating chamber 4 and smokeable material 5 as previously described with reference to FIG. 2, the heat shield 100 may comprise a cylindrical layer of heat reflective material which is located co-axially around the heating chamber 4 and co-axially inside of the heater 3. The heat shield 100 may additionally or alternatively comprise a heat-insulating layer configured to insulate the heater 3 from the smokeable material 5.

The heat shield 100 comprises a substantially heat-transparent window 101 which allows thermal energy to propagate through the window 101 and into the heating chamber 4 and smokeable material 5. Therefore, the section of smokeable material 5 which is aligned with the window 101 is heated whilst the remainder of the smokeable material 5 is not. The heat shield 100 and window 101 may be rotatable or otherwise moveable with respect the smokeable material 5 so that different sections of the smokeable material 5 can be selectively and individually heated by rotating or moving the heat shield 100 and window 101. The effect is similar to the effect provided by selectively and individually activating the heating regions 10 referred to above. For example, the heat shield 100 and window 101 may be rotated or otherwise moved incrementally in response to a signal from the puff detector 13. Additionally or alternatively, the heat shield 100 and window 101 may be rotated or otherwise moved incrementally in response to a predetermined heating period having elapsed. Movement or rotation of the heat shield 100 and window 101 may be controlled by electronic signals from the controller 12. The relative rotation or other movement of the heat shield 100/window 101 and smokeable material 5 may be driven by a stepper motor 3c under the control of the controller 12. This is illustrated in FIG. 15. Alternatively, the heat shield 100 and window 101 may be manually rotated using a user control such as an actuator on the housing 7. The heat shield 100 does not need to be cylindrical and may optionally comprise one or more suitably positioned longitudinally extending elements and or/plates.

It will be appreciated that a similar result can be obtained by rotating or moving the smokeable material 5 relative to the heater 3, heat shield 100 and window 101. For example, the heating chamber 4 may be rotatable around the heater 3. If this is the case, the above description relating to movement of the heat shield 100 can be applied instead to movement of the heating chamber 4 relative to the heat shield 100.

The heat shield 100 may comprise a coating on the longitudinal surface of the heater 3. In this case, an area of the heater's surface is left uncoated to form the heat-transparent window 101. The heater 3 can be rotated or otherwise moved, for example under the control of the controller 12 or user controls, to cause different sections of the smokeable material 5 to be heated. Alternatively, the heat shield 100 and window 101 may comprise a separate shield 3a which is rotatable or otherwise moveable relative to both the heater 3 and the smokeable material 5 under the control of the controller 12 or other user controls.

Figure 7:
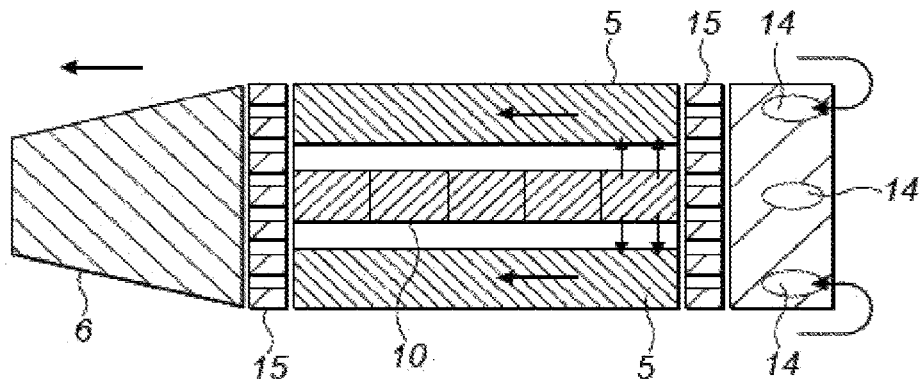
FIG. 7 is a schematic illustration of a gaseous flow through an apparatus configured to heat smokeable material.

The apparatus 1 may comprise air inlets 14 which allow external air to be drawn into the housing 7 and through the heated smokeable material 5 during puffing. The air inlets 14 may comprise apertures 14 in the housing 7 and may be located upstream from the smokeable material 5 and heating chamber 4 towards the first end 8 of the housing 7. This is shown in FIG. 2. Another example is shown in FIG. 7. Air drawn in through the inlets 14 travels through the heated smokeable material 5 and therein is enriched with smokeable material vapors, such as aroma vapors, before being inhaled by the user at the mouthpiece 6. Optionally, as shown in FIG. 7, the apparatus 1 may comprise a heat exchanger 15 configured to warm the air before it enters the smokeable material 5 and/or to cool the air before it is drawn through the mouthpiece 6. For example, the heat exchanger 15 may be configured to use heat extracted from the air entering the mouthpiece 6 to warm new air before it enters the smokeable material 5.

The apparatus 1 may comprise a smokeable material compressor 16 configured to cause the smokeable material 5 to compress upon activation of the compressor 16. The apparatus 1 can also comprise a smokeable material expander 17 configured to cause the smokeable material 5 to expand upon activation of the expander 17. The compressor 16 and expander 17 may, in practice, be implemented as the same unit as will be explained below. The smokeable material compressor 16 and expander 17 may optionally operate under the control of the controller 12. In this case, the controller 12 is configured to send a signal, such as an electrical signal, to the compressor 16 or expander 17 which causes the compressor 16 or expander 17 to respectively compress or expand the smokeable material 5. Alternatively, the compressor 16 and expander 17 may be actuated by a user of the apparatus 1 using a manual control on the housing 7 to compress or expand the smokeable material 5 as required.

The compressor 16 is principally configured to compress the smokeable material 5 and thereby increase its density during heating. Compression of the smokeable material increases the thermal conductivity of the body of smokeable material 5 and therefore provides a more rapid heating and consequent rapid volatilization of nicotine and other aromatic compounds. This allows the nicotine and aromatics to be inhaled by the user without substantial delay in response to detection of a puff Therefore, the controller 12 may activate the compressor 16 to compress the smokeable material 5 for a predetermined heating period, for example one second, in response to detection of a puff. The compressor 16 may be configured to reduce its compression of the smokeable material 5, for example under the control of the controller 12, after the predetermined heating period. Alternatively, the compression may be reduced or automatically ended in response to the smokeable material 5 reaching a predetermined threshold temperature. A suitable threshold temperature may be in the range of approximately 120° C. to 250° C., or one of the other ranges discussed previously, and may be user selectable. A temperature sensor may be used to detect the temperature of the smokeable material 5.

The expander 17 is principally configured to expand the smokeable material 5 and thereby decrease its density during puffing. The arrangement of smokeable material 5 in the heating chamber 4 becomes more loose when the smokeable material 5 has been expanded and this aids the gaseous flow, for example air from the inlets 14, through the smokeable material 5. The air is therefore more able to carry the volatilized nicotine and aromatics to the mouthpiece 6 for inhalation. The controller 12 may activate the expander 17 to expand the smokeable material 5 immediately following the compression period referred to above so that air can be drawn more freely through the smokeable material 5. Actuation of the expander 17 may be accompanied by a user-audible sound or other indication to indicate to the user that the smokeable material 5 has been heated and that puffing can commence.

Figure 9:
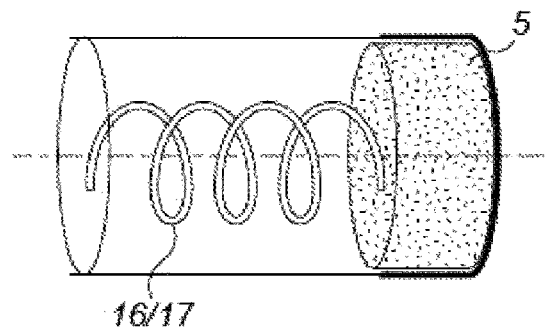
FIG. 9 is a schematic illustration of a smokeable material compressor configured to compress smokeable material during heating.
Figure 10:
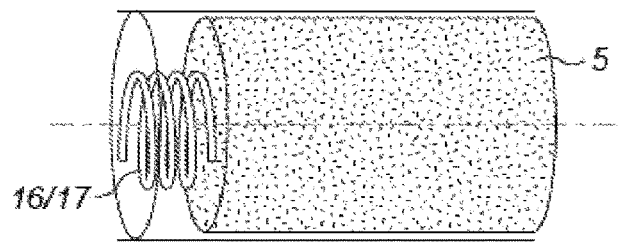
FIG. 10 is a schematic illustration of a smokeable material expander configured to expand smokeable material during puffing.
Figure 11:
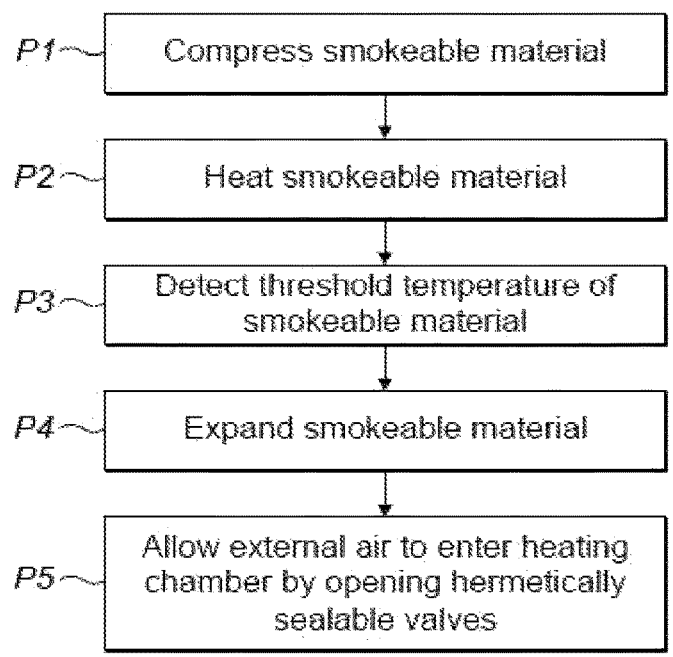
FIG. 11 is a flow diagram showing a method of compressing smokeable material during heating and expanding the smokeable material for puffing.

Referring to FIGS. 8 and 9, the compressor 16 and expander 17 may comprise a spring-actuated driving rod which is configured to compress the smokeable material 5 in the heating chamber 4 when the spring is released from compression. This is schematically illustrated in FIGS. 8 and 9, although it will be appreciated that other implementations could be used. For example, the compressor 16 may comprise a ring, having a thickness approximately equal to the tubular-shaped heating chamber 4 described above, which is driven by a spring or other means into the heating chamber 4 to compress the smokeable material 5. Alternatively, the compressor 16 may be comprised as part of the heater 3 so that the heater 3 itself is configured to compress and expand the smokeable material 5 under the control of the controller 12. A method of compressing and expanding the smokeable material 5 is shown in FIG. 11. The method comprises a first step P1 of compressing the smokeable material 5 in its heating chamber 4, a second step P2 of heating the compressed smokeable material 5, a third step P3 of detecting a threshold temperature in the smokeable material 5, a fourth step S4 of expanding the smokeable material 5, for example by releasing the compression force, and a fifth step S5 of allowing external air to enter the smokeable material heating chamber 4, for example by opening hermetically sealable inlet and outlet valves 24.

The heater 3 may be integrated with the thermal insulation 18 mentioned previously. For example, referring to FIG. 2, the thermal insulation 18 may comprise a substantially elongate, hollow body, such as a substantially cylindrical tube of insulation 18, which is located co-axially around the heating chamber 4 and into which the heating regions 10 are integrally located. The thermal insulation 18 may comprise a layer in which recesses are provided in the inwardly facing surface profile 21. Heating regions 10 are located in these recesses so that the heating regions 10 face the smokeable material 5 in the heating chamber 4. The surfaces of the heating regions 10 which face the heating chamber 4 may be flush with the inside surface 21 of the thermal insulation 18 in regions of the insulation 18 which are not recessed.

The integration of the heater 3 with the thermal insulation 18 means that the heating regions 10 are substantially surrounded by the insulation 18 on all sides of the heating regions 10 other than those which face inwardly towards the smokeable material heating chamber 4. As such, heat emitted by the heater 3 is concentrated in the smokeable material 5 and does not dissipate into other parts of the apparatus 1 or into the atmosphere outside the housing 7.

Integration of the heater 3 with the thermal insulation 18 may also reduce the thickness of the combination of heater 3 and thermal insulation 18. This can allow the diameter of the apparatus 1, in particular the external diameter of the housing 7, to be further reduced. Alternatively, the reduction in thickness provided by the integration of the heater 3 with the thermal insulation 18 can allow a wider smokeable material heating chamber 4 to be accommodated in the apparatus 1, or the introduction of further components, without any increase in the overall width of the housing 7.

Alternatively, the heater 3 may be located adjacent the insulation 18 rather than being integrated into it. For example, if the heater 3 is located externally of the heating chamber 4 as shown in FIG. 2, the insulation 18 may be located around the outside of the heater 3 so that the inwardly-facing surface 21 of the insulation faces the heater 3. If the heater 3 is located internally of the heating chamber 4, the heater 3 may be located around the outwardly-facing surface 22 of the insulation 18.

Optionally, a barrier may be present between the heater 3 and the insulation 18. For example, a layer of stainless steel may be present between the heater 3 and the insulation 18. The barrier may comprise a stainless steel tube which fits between the heater 3 and the insulation 18. The thickness of the barrier may be small so as not to substantially increase the dimensions of the apparatus. An example thickness is between approximately 0.1 mm and 1.0 mm.

Additionally, a heat reflecting layer may be present between the transverse surfaces of the heating regions 10. The arrangement of the heating regions 10 relative to each other may be such that thermal energy emitted from each one of the heating regions 10 does not substantially heat the neighboring heating regions 10 and instead travels predominately inwardly from the circumferential surface of the heating region 10 into the heating chamber 4 and smokeable material 5. Each heating region 10 may have substantially the same dimensions as the other regions 10.

The heater 3 may be bonded or otherwise secured in the apparatus 1 using pressure sensitive adhesive. For example, the heater 3 may be adhered to the insulation 18 or barrier referred to above using pressure sensitive adhesive. The heater 3 may alternatively be adhered to the cartridge 11 or an exterior surface of the smokeable material heating chamber 4.

As an alternative to the use of pressure sensitive adhesive, the heater 3 may be secured in position in the apparatus 1 using self-fusing tape or by clamps which clamp the heater 3 in place. All of these methods provide a secure fixing for the heater 3 and allow effective heat transfer from the heater 3 to the smokeable material 5. Other types of fixing are also possible.

The thermal insulation 18, which is provided between the smokeable material 5 and an external surface 19 of the housing 7, as described above, reduces heat loss from the apparatus 1 and therefore improves the efficiency with which the smokeable material 5 is heated. For example, referring to FIG. 2, a wall of the housing 7 may comprise a layer of insulation 18 which extends around the outside of the heating chamber 4. The insulation layer 18 may comprise a substantially tubular length of insulation 18 located co-axially around the heating chamber 4 and smokeable material 5. This is shown in FIG. 2. It will be appreciated that the insulation 18 could also be comprised as part of the smokeable material cartridge 11, in which it would be located co-axially around the outside of the smokeable material 5.

Figure 12:
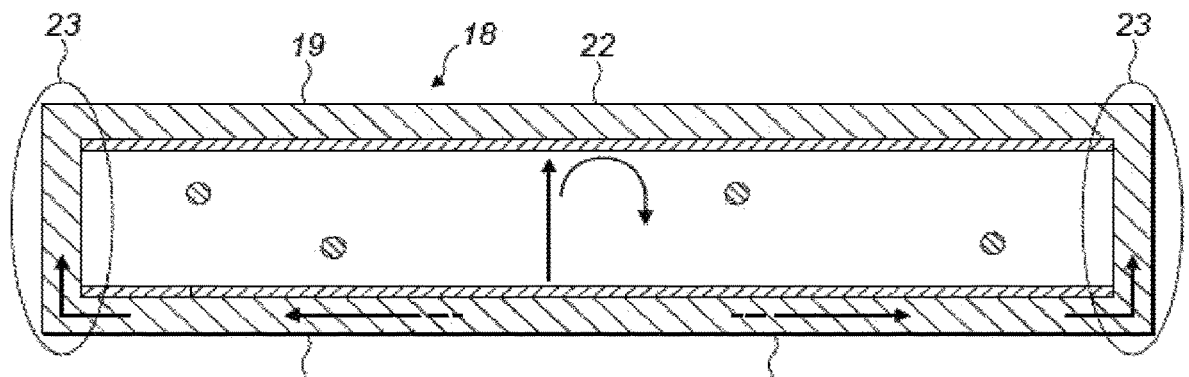
FIG. 12 is a schematic, cross-sectional illustration of a section of vacuum insulation configured to insulate heated smokeable material from heat loss.

Referring to FIG. 12, the insulation 18 may comprise vacuum insulation 18. For example, the insulation 18 may comprise a layer which is bounded by a wall material 19 such as a metallic material. An internal region or core 20 of the insulation 18 may comprise an open-cell porous material, for example comprising polymers, aerogels or other suitable material, which is evacuated to a low pressure. The pressure in the internal region 20 may be in the range of 0.1 to 0.001 mbar. The wall 19 of the insulation 18 is sufficiently strong to withstand the force exerted against it due to the pressure differential between the core 20 and external surfaces of the wall 19, thereby preventing the insulation 18 from collapsing. The wall 19 may, for example, comprise a stainless steel wall 19 having a thickness of approximately 100 μm. The thermal conductivity of the insulation 18 may be in the range of 0.004 to 0.005 W/mK. The heat transfer coefficient of the insulation 18 may be between approximately 1.10 W/(m²K) and approximately 1.40 W/(m²K) within a temperature range of between approximately 150 degrees Celsius and approximately 250 degrees Celsius. The gaseous conductivity of the insulation 18 is negligible. A reflective coating may be applied to the internal surfaces of the wall material 19 to minimize heat losses due to radiation propagating through the insulation 18. The coating may, for example, comprise an aluminum IR reflective coating having a thickness of between approximately 0.3 µm and 1.0 µm. The evacuated state of the internal core region 20 means that the insulation 18 functions even when the thickness of the core region 20 is very small. The insulating properties are substantially unaffected by its thickness. This helps to reduce the overall size of the apparatus 1.

As shown in FIG. 12, the wall 19 may comprise an inwardly-facing section 21 and an outwardly-facing section 22. The inwardly-facing section 21 substantially faces the smokeable material 5 and heating chamber 4. The outwardly-facing section 22 substantially faces the exterior of the housing 7. During operation of the apparatus 1, the inwardly-facing section 21 may be warmer due to the thermal energy originating from the heater 3, whilst the outwardly-facing section 22 is cooler due to the effect of the insulation 18. The inwardly-facing section 21 and the outwardly-facing section 22 may, for example, comprise substantially parallel longitudinally-extending walls 19 which are at least as long as the heater 3. The internal surface of the outwardly-facing wall section 22, i.e. the surface facing the evacuated core region 20, may comprise a coating for absorbing gas in the core 20. A suitable coating is a titanium oxide film.

The thermal insulation 18 may comprise hyper-deep vacuum insulation such as an Insulon® Shaped-Vacuum Thermal Barrier as described in U.S. Pat. No. 7,374,063. The overall thickness of such insulation 18 may be extremely small. An example thickness is between approximately 1 mm and approximately 1 µm, such as approximately 0.1 mm, although other larger or smaller thicknesses are also possible. The thermally insulating properties of the insulation 18 are substantially unaffected by its thickness and therefore thin insulation 18 can be used without any substantial additional heat loss from the apparatus 1. The very small thickness of the thermal insulation 18 may allow the size of the housing 7 and apparatus 1 as a whole to be reduced beyond the sizes previously discussed and may allow the thickness, for example the diameter, of the apparatus 1 to be approximately equal to smoking articles such as cigarettes, cigars and cigarillos. The weight of the apparatus 1 may also be reduced, providing similar benefits to the size reductions discussed above.

Although the thermal insulation 18 described previously may comprise a gas-absorbing material to maintain or aid with creation of the vacuum in the core region 20, a gas absorbing material is not used in the deep-vacuum insulation 18. The absence of the gas absorbing material aids with keeping the thickness of the insulation 18 very low and thus helps to reduce the overall size of the apparatus 1.

Figure 17:
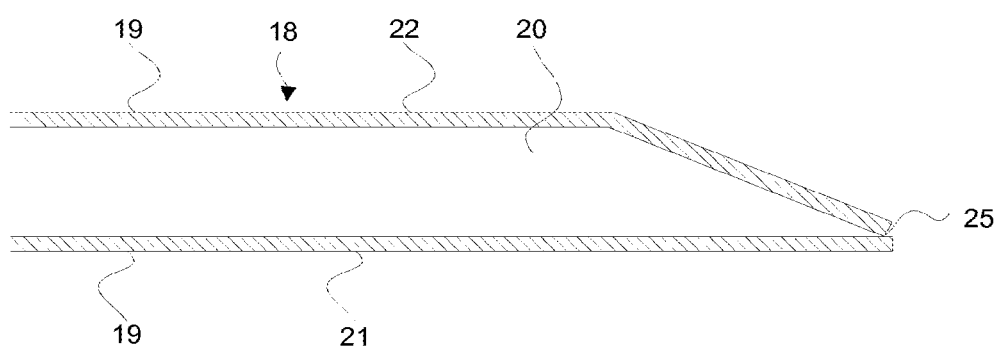
FIG. 17 is a schematic, cross sectional illustration of a partial section of deep-vacuum insulation configured to thermally insulate an apparatus configured to heat smokeable material.

The geometry of the hyper-deep insulation 18 allows the vacuum in the insulation to be deeper than the vacuum used to extract molecules from the core region 20 of the insulation 18 during manufacture. For example, the deep vacuum inside the insulation 18 may be deeper than that of the vacuum-furnace chamber in which it is created. The vacuum inside the insulation 18 may, for example, be of the order $10^{-7}$ Torr. Referring to FIG. 17, an end of the core region 20 of the deep-vacuum insulation 18 may taper as the outwardly facing section 22 and inwardly facing section 21 converge to an outlet 25 through which gas in the core region 20 may be evacuated to create a deep vacuum during manufacture of the insulation 18. FIG. 17 illustrates the outwardly facing section 22 converging towards the inwardly facing section 21 but a converse arrangement, in which the inwardly facing section 21 converges to the outwardly facing section 22, could alternatively be used. The converging end of the insulating wall 19 is configured to guide gas molecules in the core region 20 out of the outlet 25 and thereby create a deep vacuum in the core 20. The outlet 25 is sealable so as to maintain a deep vacuum in the core region 20 after the region 20 has been evacuated. The outlet 25 can be sealed, for example, by creating a brazed seal at the outlet 25 by heating brazing material at the outlet 25 after gas has been evacuated from the core 20. Alternative sealing techniques could be used.

In order to evacuate the core region 20, the insulation 18 may be placed in a low pressure, substantially evacuated environment such as a vacuum furnace chamber so that gas molecules in the core region 20 flow into the low pressure environment outside the insulation 18. When the pressure inside the core region 20 becomes low, the tapered geometry of the core region 20, and in particular the converging sections 21, 22 referred to above, becomes influential in guiding remaining gas molecules out the core 20 via the outlet 25. Specifically, when the gas pressure in the core region 20 is low, the guiding effect of the converging inwardly and outwardly facing sections 21, 22 is effective to channel the remaining gas molecules inside the core 20 towards the outlet 25 and make the probability of gas exiting the core 20 higher than the probability of gas entering the core 20 from the external, low pressure environment. In this way, the geometry of the core 20 allows the pressure inside the core 20 to be reduced below the pressure of the environment outside the insulation 18.

Optionally, as previously described, one or more low emissivity coatings may be present on the internal surfaces of the inwardly and outwardly facing sections 21, 22 of the wall 19 in order to substantially prevent heat losses by radiation.

Although the shape of the insulation 18 is generally described herein as substantially cylindrical or similar, the thermal insulation 18 could be another shape, for example in order to accommodate and insulate a different configuration of the apparatus 1 such as different shapes and sizes of heating chamber 4, heater 3, housing 7 or energy source 2. For example, the size and shape of deep-vacuum insulation 18 such as an Insulon® Shaped-Vacuum Thermal Barrier referred to above is substantially unlimited by its manufacturing process. Suitable materials for forming the converging structure described above include ceramics, metals, metalloids and combinations of these.

Figure 13:
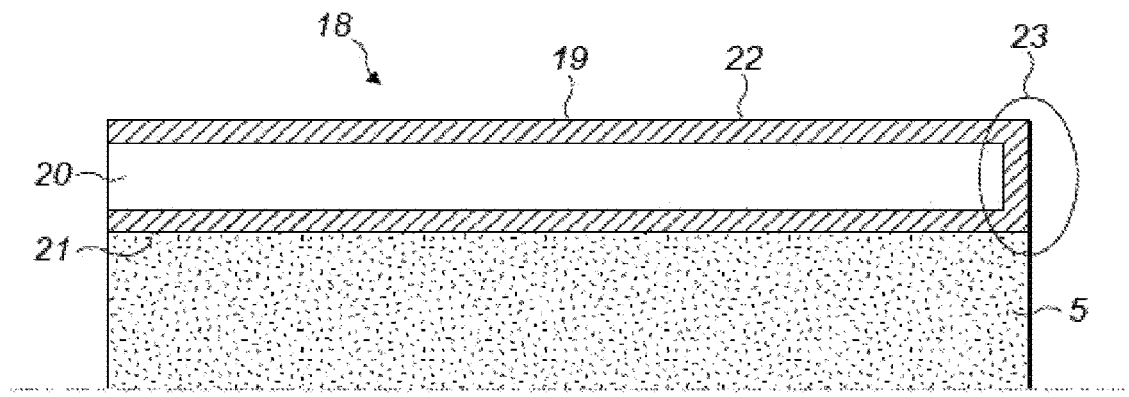
FIG. 13 is another schematic, cross-sectional illustration of a section of vacuum insulation configured to insulate heated smokeable material from heat loss.

Referring to the schematic illustration in FIG. 13, a thermal bridge 23 may connect the inwardly-facing wall section 21 to the outwardly-facing wall section 22 at one or more edges of the insulation 18 in order to completely encompass and contain the low pressure core 20. The thermal bridge 23 may comprise a wall 19 formed of the same material as the inwardly and outwardly-facing sections 21, 22. A suitable material is stainless steel, as previously discussed. The thermal bridge 23 has a greater thermal conductivity than the insulating core 20 and therefore may undesirably conduct heat out of the apparatus 1 and, in doing so, reduce the efficiency with which the smokeable material 5 is heated.

Figure 14:
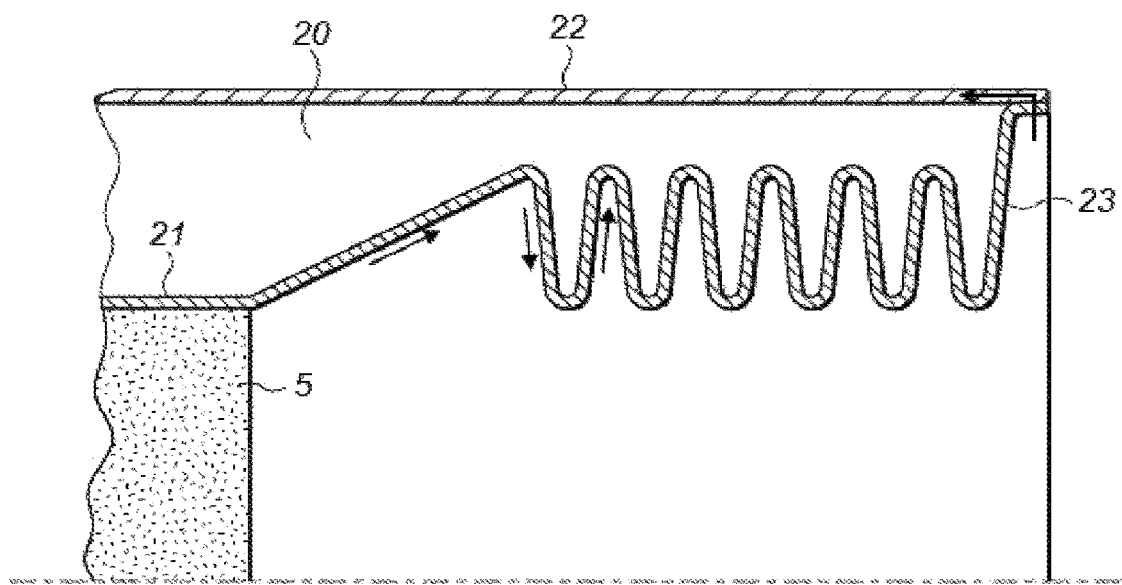
FIG. 14 is a schematic, cross-sectional illustration of a heat resistive thermal bridge which follows an indirect path from a higher temperature insulation wall to a lower temperature insulation wall.

To reduce heat losses due to the thermal bridge 23, the thermal bridge 23 may be extended to increase its resistance to heat flow from the inwardly-facing section 21 to the outwardly-facing section 22. This is schematically illustrated in FIG. 14. For example, the thermal bridge 23 may follow an indirect path between the inwardly-facing section 21 of wall 19 and the outwardly-facing section 22 of wall 19. This may be facilitated by providing the insulation 18 over a longitudinal distance which is longer than the lengths of the heater 3, heating chamber 4 and smokeable material 5 so that the thermal bridge 23 can gradually extend from the inwardly-facing section 21 to the outwardly-facing section 22 along the indirect path, thereby reducing the thickness of the core 20 to zero, at a longitudinal location in the housing 7 where the heater 3, heating chamber 4 and smokeable material 5 are not present.

Figure 16:
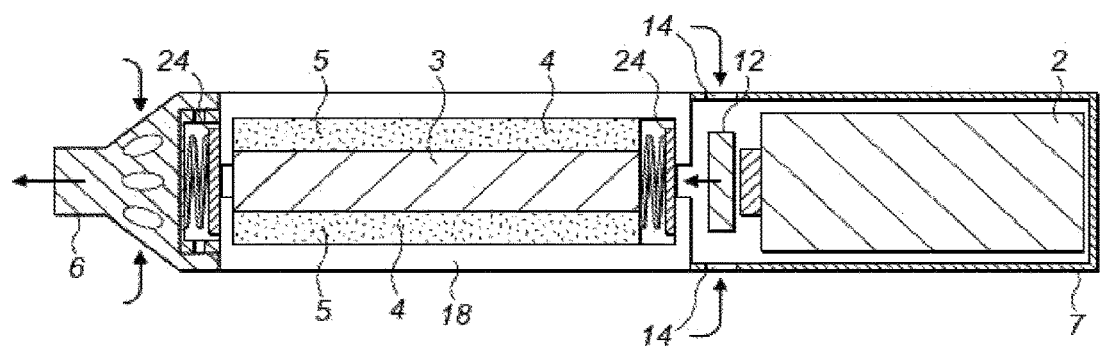
FIG. 16 is schematic, cross sectional illustration of part of an apparatus configured to heat smokeable material, in which a heating chamber is hermetically sealable by check valves.

Referring to FIG. 16, as previously discussed, the heating chamber 4 insulated by the insulation 18 may comprise inlet and outlet valves 24 which hermetically seal the heating chamber 4 when closed. The valves 24 can thereby prevent air from undesirably entering and exiting the chamber 4 and can prevent smokeable material flavors from exiting the chamber 4. The inlet and outlet valves 24 may, for example, be provided in the insulation 18. For example, between puffs, the valves 24 may be closed by the controller 12 so that all volatilized substances remain contained inside the chamber 4 in-between puffs. The partial pressure of the volatilized substances between puffs reaches the saturated vapour pressure and the amount of evaporated substances therefore depends only on the temperature in the heating chamber 4. This helps to ensure that the delivery of volatilized nicotine and aromatic compounds remains constant from puff to puff. During puffing, the controller 12 is configured to open the valves 24 so that air can flow through the chamber 4 to carry volatilized smokeable material components to the mouthpiece 6. A membrane can be located in the valves 24 to ensure that no oxygen enters the chamber 4. The valves 24 may be breath-actuated so that the valves 24 open in response to detection of a puff at the mouthpiece 6. The valves 24 may close in response to a detection that a puff has ended. Alternatively, the valves 24 may close following the elapse of a predetermined period after their opening. The predetermined period may be timed by the controller 12. Optionally, a mechanical or other suitable opening/closing means may be present so that the valves 24 open and close automatically. For example, the gaseous movement caused by a user puffing on the mouthpiece 6 may be used to open and close the valves 24. Therefore, the use of the controller 12 is not necessarily required to actuate the valves 24.

The mass of the smokeable material 5 which is heated by the heater 3, for example by each heating region 10, may be in the range of 0.2 to 1.0 g. The temperature to which the smokeable material 5 is heated may be user controllable, for example to any temperature within the temperature range of 120° C. to 250° C. as previously described. The mass of the apparatus 1 as a whole may be in the range of 70 to 125 g, although the mass of the apparatus 1 can be lower when incorporating the type of heater 3 described above and/or deep-vacuum insulation 18. A battery 2 with a capacity of 1000 to 3000 mAh and voltage of 3.7V can be used. The heating regions 10 may be configured to individually and selectively heat between approximately 10 and 40 sections of smokeable material 5 for a single cartridge 11.

It will be appreciated that any of the alternatives described above can be used singly or in combination.

In order to address various issues and advance the art, the entirety of this disclosure shows by way of illustration various embodiments in which the claimed invention(s) may be practiced and provide for superior apparatus. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. An apparatus comprising:
    a smokeable material heating chamber configured to contain a body of smokeable material during heating; and
    a heater arranged to heat smokeable material, wherein the heater comprises a substrate and at least one heating element embedded in the substrate so as to heat the substrate to cause the substrate to volatilize at least one component of the smokeable material for inhalation,
    wherein the smokeable material heating chamber is located around the heater such that the heater emits heat in a radially outward direction into the smokeable material heating chamber,
    wherein the heater has peripheral surfaces, and wherein the heater is arranged such that the peripheral surfaces of the heater principally comprise those of the substrate such that the smokeable material is heated principally by heat emitted from the heated substrate rather than being heated directly by the at least one heating element,
    wherein the heating element is arranged to heat the substrate to a temperature sufficient for the substrate to volatilize at least one component of the smokeable material, and
    wherein the rate at which the temperature of the substrate increases during heating is substantially the same as the rate at which the temperature of the at least one heating element increases.

2. An apparatus according to claim 1, wherein the coefficient of thermal expansion of the heating element is substantially equal to the coefficient of thermal expansion of the substrate.

3. An apparatus according to claim 1, wherein the heating element and the substrate are sintered to form a chemically bonded structure.

4. An apparatus according to claim 1, wherein the substrate comprises a ceramics material and the heating element comprises an electrically resistive trace material.

5. An apparatus according to claim 1, comprising a plurality of the heating elements arranged in layers inside the substrate.

6. An apparatus according to claim 5, wherein the layers of heating elements are interconnected by heating element vias through the substrate.

7. An apparatus according to claim 1, configured to heat the smokeable material to a smokeable material volatilizing temperature of at least 120 degrees Celsius.

8. An apparatus according to claim 1, configured to heat the smokeable material to a smokeable material volatilizing temperature of between 120 degrees Celsius and 250 degrees Celsius.

9. An apparatus according to claim 1, configured to heat the smokeable material to a smokeable material volatilizing temperature of between 130 degrees Celsius and 180 degrees Celsius.

10. An apparatus according to claim 1, wherein the at least one heating element is a printed heating element and wherein the at least one electrical circuit is a printed electrical circuit.

11. An apparatus according to claim 1, wherein the temperature measurement circuit comprises a resistance temperature detector.

12. An apparatus according to claim 1, wherein the heater comprises at least one electrical circuit embedded in the substrate to provide control signals or measurement signals to a controller of the apparatus, wherein the at least one electrical circuit comprises a temperature measurement circuit embedded in the substrate, and wherein the temperature measurement circuit is located on, adjacent to or underneath the at least one heating element.

13. Use of an apparatus comprising a smokeable material heating chamber configured to contain a body of smokeable material during heating and a heater comprising a substrate and at least one heating element embedded in the substrate to heat the substrate and cause the substrate to volatilize at least one component of smokeable material for inhalation, wherein the smokeable material heating chamber is located around the heater such that the heater emits heat in a radially outward direction into the smokeable material heating chamber, wherein the heater has peripheral surfaces, and wherein the heater is arranged such that the peripheral surfaces of the heater principally comprise those of the substrate such that the smokeable material is heated principally by heat emitted from the heated substrate rather than being heated directly by the at least one heating element;

wherein the heating element is arranged to heat the substrate to a temperature sufficient for the substrate to volatilize at least one component of the smokeable material; and wherein the rate at which the temperature of the substrate increases during heating is substantially the same as the rate at which the temperature of the at least one heating element increases.

* * * * *